United States Patent [19]

Englund et al.

[11] Patent Number: 5,197,474

[45] Date of Patent: Mar. 30, 1993

[54] PATIENT BED IN A MAGNETIC RESONANCE IMAGING APPARATUS

[75] Inventors: Rurik Englund, Espoo; Pentti Nummi, Kerava; Maija Nurmirinta, Hyvinkää ; Markku Seppänen, Helsinki; Matti Smalén, Klaukkala; Juha Virtanen, Helsinki; Yrjö Yrjölä, Vantaa, all of Finland

[73] Assignee: Instrumentarium Corp., Finland

[21] Appl. No.: 693,665

[22] Filed: Apr. 30, 1991

[30] Foreign Application Priority Data

Jun. 14, 1990 [FI] Finland ................. 902978

[51] Int. Cl.$^5$ ............................. A61B 5/055
[52] U.S. Cl. ................... 128/653.5; 324/318; 5/601
[58] Field of Search .......... 128/653.2, 653.5; 269/322-328; 324/318; 5/600, 601

[56] References Cited

U.S. PATENT DOCUMENTS

| | | | |
|---|---|---|---|
| 4,475,072 | 10/1984 | Schwehr et al. ...................... | 5/601 |
| 4,638,252 | 1/1987 | Bradshaw ........................... | 128/653 |
| 4,641,823 | 2/1987 | Bergman ........................... | 269/322 |
| 4,805,626 | 2/1989 | DiMassimo et al. ................ | 128/653 |
| 5,007,425 | 4/1991 | Vanek et al. ....................... | 128/653.5 |
| 5,066,915 | 11/1991 | Omori et al. ........................ | 324/318 |

Primary Examiner—Ruth S. Smith
Attorney, Agent, or Firm—Andrus, Sceales, Starke & Sawall

[57] ABSTRACT

A mechanism for transporting a patient to a magnetic resonance unit. A coil seat is mounted on the upper surface of a lower bed and the lower bed is mounted for movement relative to a magnet. An upper bed is mounted for movement on the lower bed. In the positioning stage, the coil is located outside of the magnet and the upper bed carrying a patient is moved relative to the lower bed to position the patient in registry with the coil, such that a desired anatomical area is brought into the imaging area of the coil. This is followed by pushing the upper and lower beds as a unit into the bore of the magnet. As various coils can be positioned on the lower bed at a common positioning location, it is possible to employ a common electric connection to eliminate the need for separately attachable cables.

6 Claims, 4 Drawing Sheets

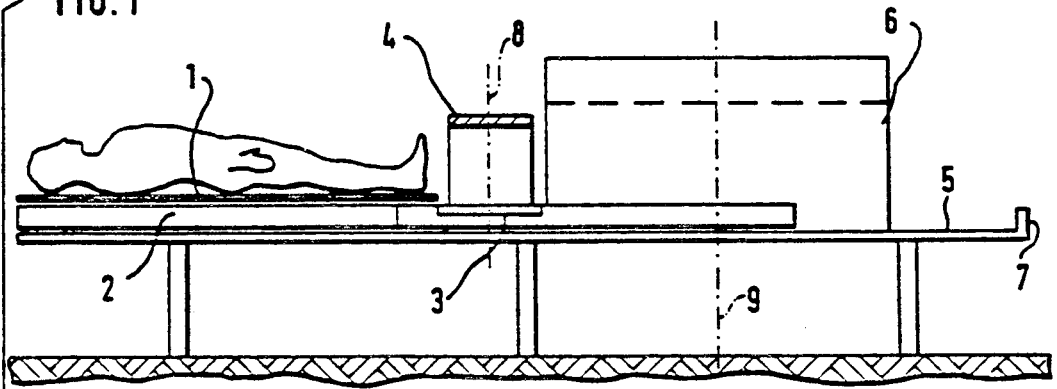
STEP a) POSITIONING OF PATIENT AND COIL ON BED
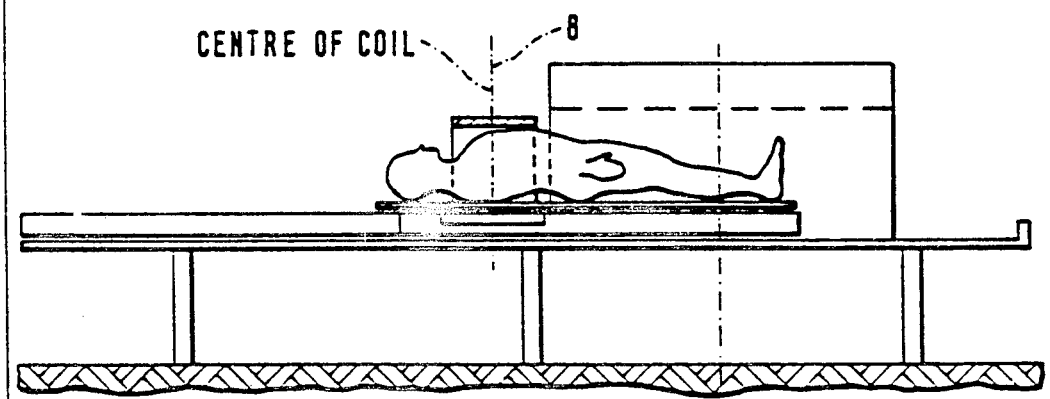
STEP b) POSITIONING OF PATIENT RELATIVE TO COIL
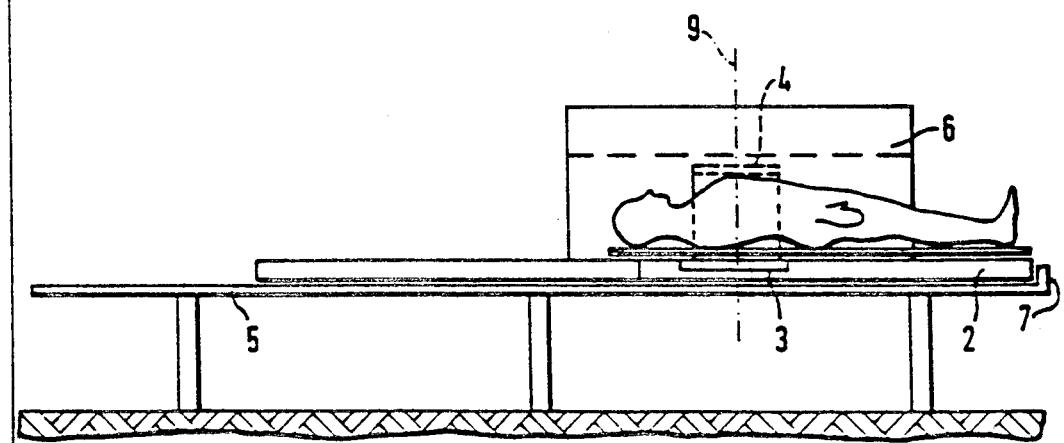
STEP c) IMAGING POSITION
FIG. 1 — PATIENT'S BED IN MAGNETIC RESONANCE IMAGING APPARATUS. THE COIL IS A BODY COIL.

FIG. 2 PATIENT'S BED WHEN USING BACK COIL.
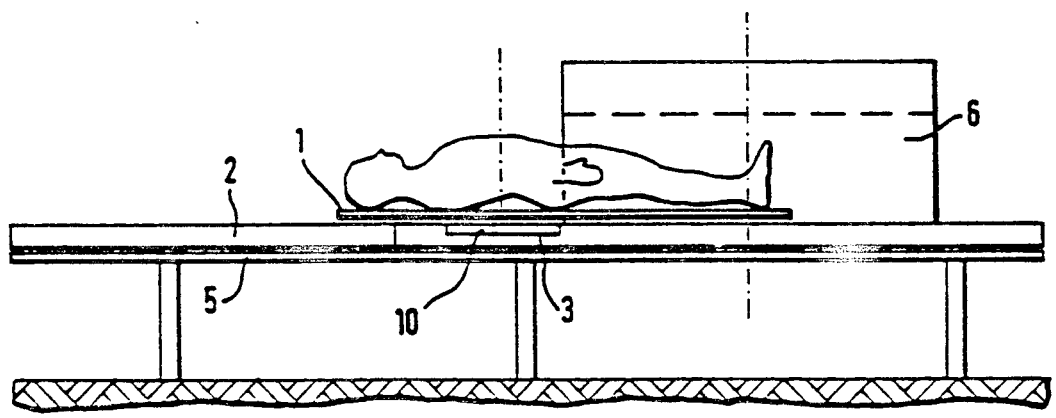
STEP a) POSITIONING OF PATIENT RELATIVE TO COIL
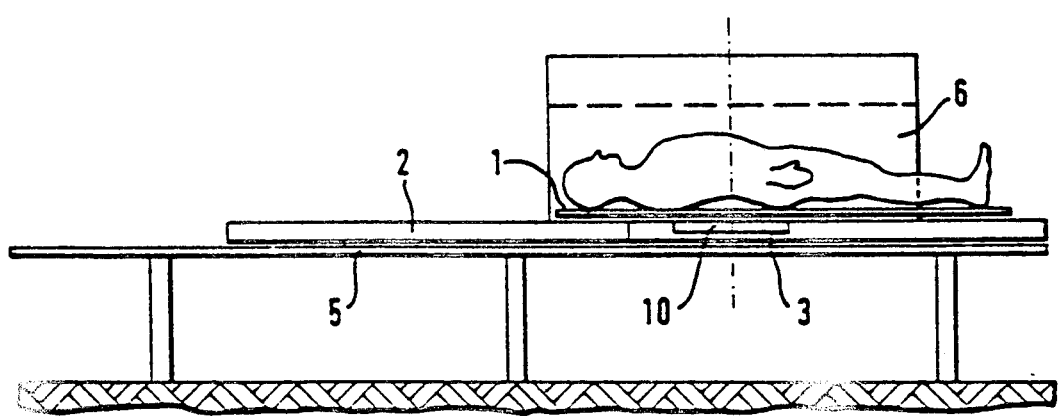
STEP b) IMAGING POSITION

KNEE COIL

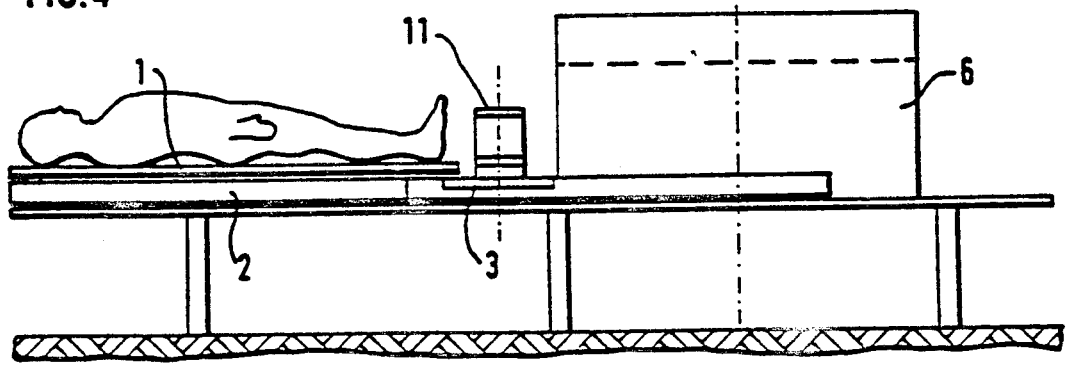
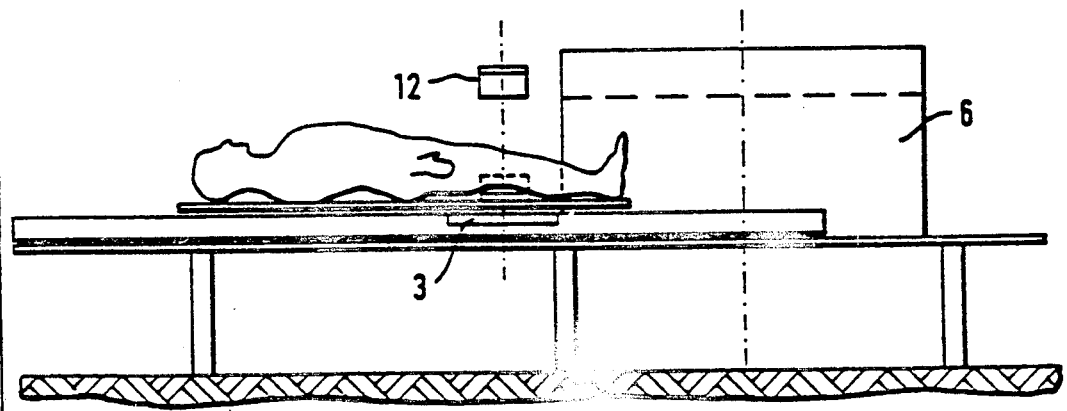
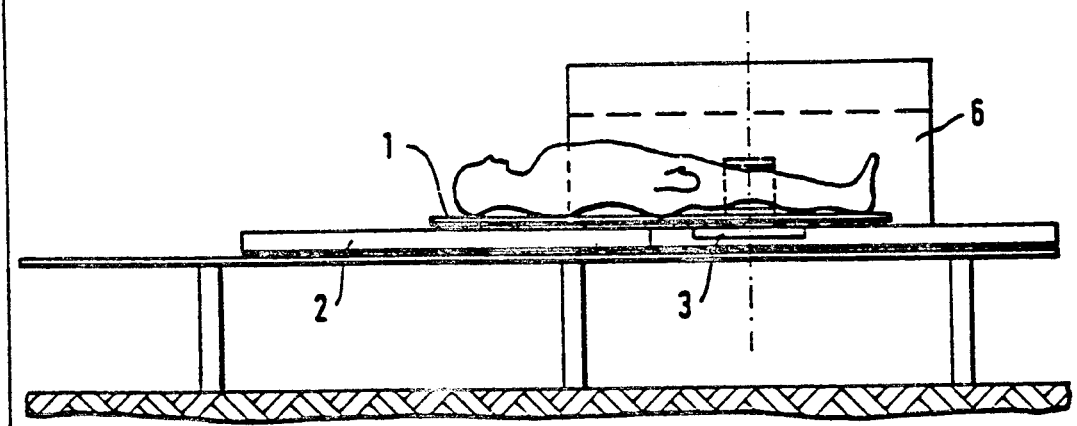

PATIENT BED IN A MAGNETIC RESONANCE IMAGING APPARATUS

The present invention relates to a patient bed in a magnetic resonance imaging apparatus for bringing a patient to be examined into an imaging zone located inside a magnet included in the imaging apparatus. An rf (radio frequency) coil, required in the imaging process and a plurality of which are included in the apparatus, is also mounted on the bed.

BACKGROUND OF THE INVENTION

A patient bed required in magnetic resonance imaging equipment is in a per se known manner used not only to support a patient in a position required by imaging but also as a platform for the accessories needed during an imaging process. The most important of such accessories or facilities is an rf-coil, required for receiving an NMR (nuclear magnetic resonance) signal originating from a patient. Sometimes the same coil is also used for transmitting an excitation pulse required for producing a signal. This is often effected by means of a separate transmission coil which can be placed either inside the magnet or on the patient's bed. Other accessories include e.g. various cushions, supports and attachment belts for a patient's comfort and a proper imaging position. In addition, a patient bed must be capable of performing a variety of positionings: positioning of a patient and a coil on the bed, positioning of a patient relative to the coil, and positioning of a patient as well as a coil relative to the magnet.

In order to optimize a signal-to-noise ratio, the rf-coils required for reception must be designed so as to surround an object to be imaged with as high a degree of filling as possible. Thus, various anatomical targets, such as the head, the neck, the knee etc., must be provided with their own separate coils which are placed on a patient bed as close to the target or object as possible or around the object.

The coils required in transmission are generally bulky in size relative to the object in order to achieve a sufficient transmission field homogeneity. Often it is sufficient to have a single common transmission coil, which is usually placed inside the magnet and which is fixed in position and detached from the patient bed. It is also possible to employ separate transmission coils, and in some cases, the transmission and reception coils can be combined to provide a single coil assembly. In these cases, the coil is positioned into the center or bore of the magnet by utilizing the bed or its platform.

A patient is positioned on the bed most often in a lying position although e.g. a wrist can be imaged by having a patient in a sitting position at the inlet opening of a magnet on a lowered bed while holding his or her hand inside the magnet. When in a lying position, a patient is usually lying on his or her back. When imaging the head and the neck, a patient is generally pushed into the magnet head first and, when imaging the lower limbs, generally feet first. Otherwise, the orientation can be freely selected, although a patient is generally pushed into the magnet head first. Positioning of a patient on the bed can be facilitated by lowering the bed for a patient to settle thereon.

The reception coil is set in position either before or after a patient is transferred onto the bed. It is necessary to preset such coils which are difficult or impossible to position afterwards relative to a patient. Such coils include e.g. a spine coil positioned underneath a patient or a neck coil placed under the neck. A drawback in these coils is that, if a coil is to be replaced, the patient must move out of the way for a replacement. In addition, the coil may get in the way during the transfer of a patient. Such coils are mounted on the bed either at a single spot or at several alternative, generally permanent locations.

It is possible to position afterwards the coils to be mounted on top of a patient or to be threaded into position or the coils to be drawn around a patient. Such coils include e.g. a heart coil to be placed on top of the thorax, a shoulder coil to be threaded into the axilla, and a head coil to be drawn around the head.

Thus, some coils can be designed in a manner that a segment of the coil is pre-mounted on the bed as a patient moves onto the bed and on top of said segment of the coil. The other coil segment is after that placed in position. This type of coil can be e.g. an openable head-, body- or knee coil. A drawback in such coils is that there is usually required an electric contact between the different segments and this can be electrically delicate or mechanically complicated to carry out. The openability may also limit the geometry of a coil. In addition, the coil segment pre-mounted on the bed may also get in the way during the move-over of a patient.

For the imaging process a patient must be positioned relative to the coil in a manner that a spot to be imaged will be located within the field of imaging as well as possible. The center of a field of imaging is generally the center of symmetry of a coil and it can be indicated by means of auxiliary markings. In order to achieve a proper positioning, the relative location of a patient and a coil must necessarily be changed, an the same applies if the location of a field of imaging should be changed during an imaging session. With fixedly positioned coils this may be inconvenient, particularly if a patient is difficult to move over. Especially spine and body imaging processes can be problematic. In spine imaging, despite a fixedly positioned casing, the imaging coil itself can be moved within the casing relative to a patient. However, this can lead to inconvenient mechanical solutions and and result in an impractically large-size coil box or casing if the mobility is to be extended over the entire spinal area.

The positioning is generally carried out with the help of tracer 8 of (FIG. 1), which indicated e.g. the location of the center of a coil. If the location of a coil on the bed is arbitrary, the coil must be provided with some kind of marking to indicate the location of the center of said coil. The marking may sometimes be hidden underneath a patient. The positioning tracers are generally located at the mouth of a magnet, which in view of a practitioner can be a cramped spot for inspecting the positionings.

As for the transmission coils, a fixed transmission coil fitted inside a magnet is the handiest alternative in view of handling a patient and the coil. If, for example due to a higher transmission field amplitude, it should be desirable to employ a smaller transmission coil, the electrical elimination of a fixed transmission coil may cause trouble. In this case, a removable transmission coil is a preferred solution. In this case, for example, a transmission coil can be inserted inside a magnet the back way, the patient's bed extending through the coil. Hence, the bed can be telescopic which sets special requirements in terms of rigidity. The bed and its platform can also be supported at its rear end, whereby a transmission coil runs within a recess underneath the bed and cleaning of such recess may prove to be a problem.

When a patient has been positioned relative to a coil, the coil and the patient must still be brought in the middle of a magnet in a manner the imaging center of a coil will be located in the center 9 (FIG. 1) of a magnet at least in longitudinal direction. If the location of a coil on the bed varies, it is necessary to employ some type of scale of length and its numerical system for bringing a coil in the middle of a magnet. An auxiliary marking on the coil and positioning tracers are generally used as a means for informing the system of the location of a coil on the bed. The numerical system of the scale is also utilized for stopping a bed relative to a magnet in a manner that the coil will be positioned in the middle of the magnet. If the magnet has a sufficiently open structure, a coil can be located right in the middle of the magnet with the positioning of a patient relative to the coil being also effected there. If the magnet is provided with a sufficiently large bore, the bed can also be moved laterally in addition to longitudinal direction.

If the location of a coil on the bed is arbitrary, the coil cables will generally be long since they must be dimensioned according to the furthest-away location whenever the bed has been pulled out of a magnet. During the movement of a bed the long cables may readily get stuck e.g. between magnet and bed unless this has been prevented by means of some kind of additional structure or unless the equipment operator guides the cables.

Generally, a single imaging apparatus is operated by employing a plurality of coil positioning techniques. This may complicate the mechanical structure of the apparatus and restrict the introduction of new types of coils. In addition, the practitioners or nurses operating the apparatus must be familiar with several different operating and positioning techniques, which is a possible cause of malfunctions especially in emergencies. A complicated structure may also result in poorer maintenance of the apparatus.

SUMMARY OF THE INVENTION

An object of the present invention is to provide a novel more ergonomic patient bed in an effort to eliminate the above drawbacks and for facilitating the handling of patient and coils as well as various positioning procedures necessary during the preparation of an imaging session as compared to the prior art constructions.

This object is achieved by means of a patient's bed of the invention included in a magnetic resonance imaging apparatus, characterized in that said bed comprises two movable sections one of which, a lower bed is provided with a positioning point or a coil seat in which rf-coils can be fitted, and the other is a upper bed movable on top of the lower bed and adapted to accommodate a patient.

BRIEF DESCRIPTION OF THE DRAWINGS

The invention will now be described in more detail with reference made to the accompanying drawings, in which FIG. 1 is a side schematic side view of a patient bed of the invention included in a magnetic resonance imaging apparatus, the coil comprising a body coil. Step a) illustrates the positioning of a patient and a coil on the bed, step b) the positioning of a patient relative to the coil, and step c) the imaging position.

FIG. 2 is a schematic side view of a patient bed when using a spine coil. Step a) illustrates the positioning of a patient relative to the coil and step b) the imaging position.

FIG. 4 is a schematic side view of a patient bed of the invention when using a knee coil as shown in FIG. 3. Step a) illustrates the positioning of a patient and a coil on the bed, step b) the positioning of a patient relative to the coil, and step c) the imaging position.

DESCRIPTION OF THE ILLUSTRATED EMBODIMENT

Figure 3:
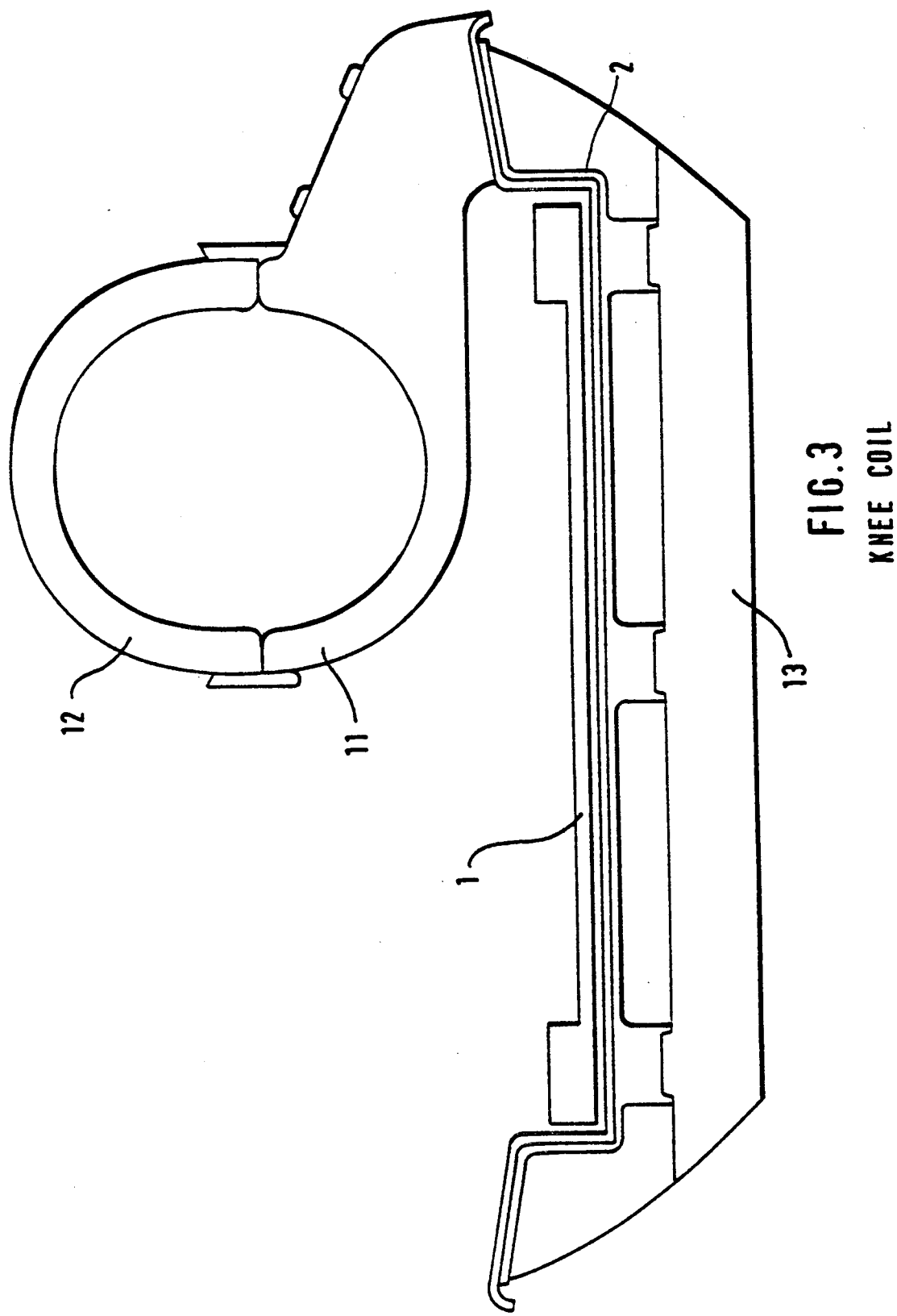
FIG. 3 shows in the longitudinal direction of a patient bed the fitting of a knee coil in connection with a patient bed of the invention.

A patient bed according to the invention is shown in FIG. 1, the coil being shown as a body coil 4 by way of an example. The patient bed comprises two movable sections: a lower and upper bed 2 and 1. The lower bed 2 travels on top of a fixed track or platform 5. The lower bed 2 is provided with coils positioned in a single positioning point, a coil seat 3. A patient lies on upper bed 1 movable on top of the lower bed. The upper and/or lower bed can be moved either manually or by means of a motor. The motor can be controlled from a control panel or from a control console included in the apparatus.

When a patient is positioned on upper bed 1, the upper bed is driven to the end of lower bed 2, the area of coil seat 3 remaining accessible. Thus, a coil 4, 10 or 11 can be positioned on the bed regardless of the patient and vice versa. The positioning of a patient relative to the coil is effected by running upper bed 1 over, through or under the coil module. A body coil 4 can be e.g. a ring-shaped piece, through which a patient is driven on upper bed 1 to a desired location. A spine coil 10 can be positioned in coil seat 3 in a manner that said upper bed 1 runs over coil 10 (FIG. 2). A knee coil 11 can be constructed in a manner that upper bed 1 travels underneath the coil (FIGS. 3 and 4). By moving upper bed 1 relative to the coil a patient or when using a knee coil, a patient's leg can be positioned in the coil at a desired location. When a patient has been positioned relative to the coil, said upper bed 1 is locked and thereafter the patient along with the coil is pushed inside a magnet 6 by means of lower bed 2.

Since the positioning locations for a coil and a patient are separated from each other, the positionings of a coil and a patient on the bed can be made independent of each other. The coil can be mounted on the lower bed, or on an insert or filling piece 13, either before or after the positioning of a patient. The replacement of a coil is also easy since a patient need not rise out of the way of a coil for a replacement. The patient can also be subjected to preparatory measures without any interference on the part of a coil.

Since all coils are mounted on the bed at the same location, there is just one positioning method which facilitates operation of the apparatus. Another result of a common positioning location is that the electric connection of a coil is readily effected directly in coil seat 3 to thus eliminate a coil connecting cable which the operator would otherwise have to couple to a contact panel included in the apparatus. Also, cables generally tend to get stuck e.g. between a movable bed and a magnet. If there is no desire to employ connection of the coil in that manner and the coil seat is located at the bore of a magnet 6, the coil will have a minimum trajectory into the center of a magnet when positioning said coil, which minimizes the length of a necessary connecting cable.

Since a patient is carried on a separate upper bed 1, the patient can be readily positioned at a desired location of the coil by moving the upper bed relative to the coil. Thus, the patient himself or herself need not move for a successful positioning which, particularly with disabled and heavy patients, facilitates the work of a person operating the apparatus. The position of a coil relative to a patient can be readily adjusted also during an imaging session. If desired, this can also be done from the apparatus' control console by operating bed-driving motors. The bed allows a patient to be carried into magnet 6 either the feet or head first. The position can be selected to be appropriate e.g. in view of coupling of external associated equipment.

The coils can be mechanically constructed in a manner that their centers of imaging are located relative to a coil seat in the axial direction of a magnet always at the same point, e.g. at the center of a coil seat. Since the center of imaging of a coil is always positioned in the middle of magnet 6, said coil seat 3 and hence also lower bed 2 are always at the same location in the magnet in imaging position. By fixing a stopper 7 included in lower bed 2 in such a manner that, upon stopping, said lower bed 2 always assumes this imaging position, there will be no need for the identification of location relative to the magnet for positioning.

The patient bed has a structure which also allows for other traditional coil positioning techniques. If necessary, a coil can also be positioned on top of an upper bed underneath a patient, e.g. a spine coil 10. The coils, which only employ a single positioning location when positioning a patient relative thereto, can be fixed directly to a patient or positioned in coil seat 3. An example of the former case is a liver coil to be worn by a patient and the latter case is exemplified by a head coil. Thus, the bed allows the use of a versatile selection of coils which can be optimized according to intended use.

FIG. 1 illustrates a body coil 4 which is generally a circular ring. Since a patient is pushed into the coil, the latter need not be openable for the positioning of a patient. Openability may lead to inconvenient mechanical solutions.

A knee coil 11 shown in FIG. 3 is only on its one side to filling piece 13 inside the coil seat 3. Thus, when a patient is moved relative to coil 11 there is no need at all for a nurse to touch the leg not being imaged. The coil 11 is provided with an openable top section 12. When a patient is moved relative to the coil, the nurse simultaneously lifts the leg to be imaged and places it inside coil 11. Following the positioning, the top coil section 12 is re-positioned. By using a suitable coil geometry the removable or otherwise openable top coil section 12 is not necessary. Coil 11 can be constructed in a fashion that it can be swung around for imaging either the right or left leg.

The transmission coil can be located inside magnet 6 or it can be a part of a coil module to be set in coil seat 3. Transmission and reception coils can also be separate, e.g. a transmission coil is set in the coil seat and a reception coil is fastened to a patient. Reception and transmission coils can also be physically the same coils. Thus, the transmission coil can be designed in a plurality of ways and optimized both in terms of electrical arrangement of a coil and coil ergonomy as desired.

In view of an effective operation of the imaging apparatus, it is preferable that the preparatory measures on a patient (including transfer of a patient onto the bed e.g. from a hospital bed) be carried out elsewhere from the immediate vicinity of the actual imaging apparatus. The forward section of lower bed 2 together with upper bed 1 can be made removable from the rest of the bed to make this possible. The remaining section of a lower bed, which is provided with coil seat 3, remains in contact with the apparatus.

We claim:

1. A magnetic resonance unit, comprising a supporting structure, a magnet mounted on the supporting structure and having a central bore, a lower bed, a coil assembly mounted in fixed relation to the upper surface of said lower bed, means for mounting said lower bed for movement relative to said supporting structure from a first location where the coil assembly is outside of said bore to a second location where the coil assembly is located within the bore of a magnet, an upper bed to support a patient, means for mounting the upper bed for movement relative to the upper surface of the lower bed whereby the upper bed can be moved relative to the lower bed when the lower bed is in the first location to position the patient in registry with the coil assembly, and means for moving the lower bed with the associated coil assembly along with the upper bed and the patient supported thereon in unison to the second location in the bore of the magnet.

2. The unit of claim 1, wherein said coil assembly has an opening with the axis of the opening disposed parallel to the axis of the bore.

3. The unit of claim 2, wherein the coil assembly is a knee coil attached to the lower bed and the opening is offset laterally from the longitudinal center line of the lower bed allowing a leg which is not being imaged to rest on the upper bed.

4. The unit of claim 3, and including a support for supporting the knee coil on the lower bed, said support extending upwardly from a side edge of the lower bed and then laterally inward over the upper bed.

5. The unit of claim 1, and including a stop mounted on the supporting structure to limit the movement of the lower bed into the bore of the magnet whereby the lower bed and its associated coil assembly is positioned at a predetermined imaging location.

6. A method of transporting a patient to a magnetic resonance unit, comprising the steps of supporting a patient on an upper movable bed, moving the upper bed to a lower bed relative to a coil mounted on said lower bed to position the patient in registry with the coil, and moving the upper bed and the lower bed in conjunction to position the coil and the patient in the bore of a magnet of a magnetic resonance unit.

* * * * *

UNITED STATES PATENT AND TRADEMARK OFFICE
CERTIFICATE OF CORRECTION

PATENT NO. : 5,197,474
DATED : March 30, 1993
INVENTOR(S) : RURIK ENGLUND ET AL

It is certified that error appears in the above-indentified patent and that said Letters Patent is hereby corrected as shown below:

Col. 6, Line 20, CLAIM 1 Cancel "to" and substitute therefor --on--; Col. 6, Line 56, CLAIM 6 Cancel "to" and substitute therefor --on--

Signed and Sealed this

Twenty-eighth Day of June, 1994

Attest:

BRUCE LEHMAN

*Attesting Officer*   *Commissioner of Patents and Trademarks*